United States Patent

Magerl et al.

(12)

(10) Patent No.: US 6,808,526 B1
(45) Date of Patent: Oct. 26, 2004

(54) OSTEOSYNTHESIS SCREW, ESPECIALLY FOR APPLICATION BY A TRANSLAMINAR VERTEBRAL SCREW

(75) Inventors: Fritz Magerl, St. Gallen (CH); Erich Wintermantel, Fislisbach (CH); Jörg Mayer, Niederlenz (CH); Roger Roland Tognini, Widnau (CH); Clemens Dransfeld, Lenzburg (CH); Walter Spirig, Platz-Walzenhausen (CH)

(73) Assignee: Sepitec Foundation, Vaduz (LI)

( * ) Notice: Subject to any disclaimer, the term of this patent is extended or adjusted under 35 U.S.C. 154(b) by 0 days.

(21) Appl. No.: 09/743,538

(22) PCT Filed: Jul. 9, 1999

(86) PCT No.: PCT/EP99/04846

§ 371 (c)(1),
(2), (4) Date: May 14, 2001

(87) PCT Pub. No.: WO00/03649

PCT Pub. Date: Jan. 27, 2000

(30) Foreign Application Priority Data

Jul. 13, 1998 (DE) .......................................... 198 31 336

(51) Int. Cl.⁷ ............................................... A61B 17/58
(52) U.S. Cl. ........................................... 606/61; 606/73
(58) Field of Search .............................. 606/65, 73, 67, 606/72

(56) References Cited

U.S. PATENT DOCUMENTS

| 4,820,098 A | * | 4/1989 | Taubert et al. | ............... | 411/411 |
|---|---|---|---|---|---|
| 5,129,901 A | | 7/1992 | Decoste | | |
| 5,375,956 A | * | 12/1994 | Pennig | ...................... | 411/389 |
| 5,672,178 A | | 9/1997 | Petersen | | |
| 5,743,912 A | * | 4/1998 | Lahille et al. | ................ | 606/65 |

FOREIGN PATENT DOCUMENTS

| DE | 3923099 | | 4/1990 | | |
|---|---|---|---|---|---|
| DE | 4307633 | | 5/1994 | | |
| EP | 0424734 | | 10/1990 | | |
| GB | 2040769 | | 9/1980 | | |
| GB | 2040769 A | * | 9/1980 | ........... | F16B/25/00 |

\* cited by examiner

Primary Examiner—Brian L. Casler
Assistant Examiner—Lina R Kontos
(74) Attorney, Agent, or Firm—Volpe and Koenig, P.C.

(57) ABSTRACT

An osteosynthesis screw (1) used especially for application by a translaminar vertebral screw, comprises a shaft (3) at least partially provided with a thread (2) and a head (4) formed at one of its ends and having a notch (5) for a tool. Said shaft (3) has a section (A) with a thread (2) on the end section oriented towards the head (4). The remaining section (B) of the shaft (3) up to the free end is produced without a thread. The head (4) has a diameter (D1) corresponding at least approximately to the outer diameter (DA) of the thread (2) and is provided with the inner notch (5) for a tool. The section (A) of the shaft (3) with the thread (2) has a configuration of uniform thickness, e.g. a trilobular configuration. Thus, the invention provides an osteosynthesis screw (1) exhibiting a short section (A) with a thread (2) and a long section (B) without a thread, said screw having a pull-out head (4) which is secured both axially and rotationally.

22 Claims, 3 Drawing Sheets

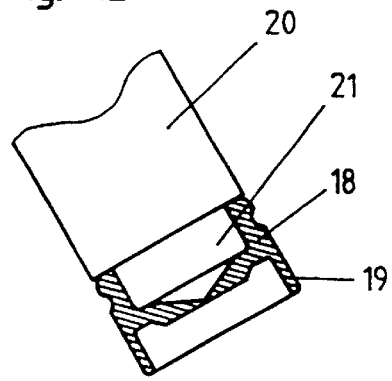
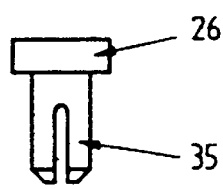
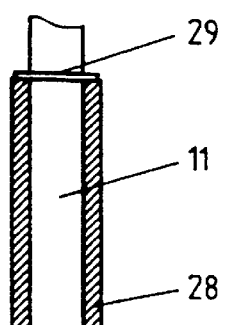
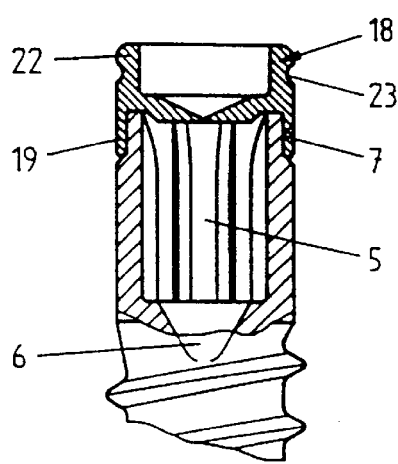
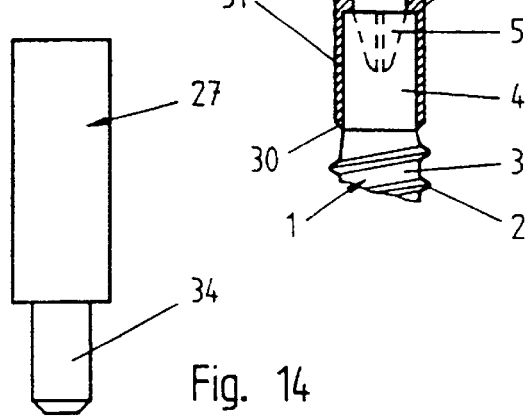
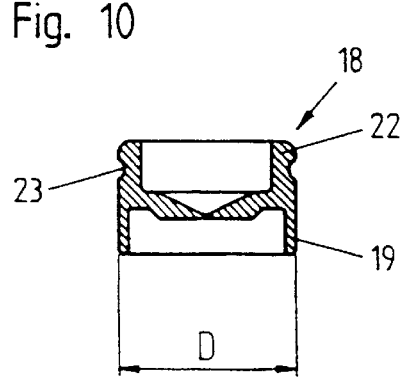
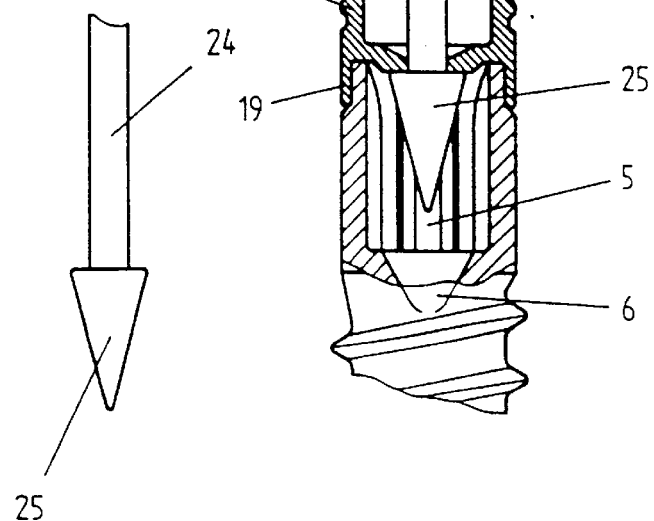

OSTEOSYNTHESIS SCREW, ESPECIALLY FOR APPLICATION BY A TRANSLAMINAR VERTEBRAL SCREW

The invention relates to an osteosynthesis screw, in particular for application in translaminar vertebral-screw fixation, with a shaft, at least partially comprising a thread, and a head formed at least at one of its ends and comprising a notch arrangement for a tool.

Translaminar screw fixation on the lumbar vertebrae in the context of spinal fusion (spondylosyndesis) and operative treatment of injuries has been used for almost twenty years. The principle of translaminar screw fixation consists of the use of osteosynthesis screws to block the zygapophyseal joints, to prevent any possible movement between vertebrae; with the resulting immobilisation of the respective section of the lumbar spine safeguarding consolidation of the spondylosyndesis or healing of the injury. The screws enter on one side of the spinous process of the bone, extend through the mutual lamina, traverse the zygapophyseal joints and end up in the base of the transverse process of the lower vertebra. The free end of the screw is then located in the ventrocaudal delimitation of the transverse process, but it must not protrude at that location.

There is only limited space available for placement of translaminar screws in the dorsal structures of the vertebrae. For anatomical reasons the tolerances are very limited in regard to the most favourable screw position both from an anatomical and a mechanical perspective. Even minor deviation from the ideal position brings about a rapid decrease in effectiveness of the respective screw. For this reason, the use of a special target device is recommended for placement of the screws.

Due to the fact that in each vertebra there is only one ideal position for each of the two translaminar screws, the problem arises in the region of the spinous process of the upper vertebra, i.e. where the screws are inserted in the bone, where they cross over, in that it is not possible to position both screws ideally. Consequently, the position of the second screw must already be considered at the time of setting the first screw. Otherwise, only a very unfavourable placement option may remain for the second screw. In particular in the case of the fifth lumbar vertebra, the positioning margin is very small.

In principle the screws act like pins that block the facet joint of the spine. Because smooth pins would slide in the bone and other alternatives have not been available, normal osteosynthesis screws with a continuous thread have been used so far. This is however associated with several disadvantages: in the case of harder bones, the thread needs to be pre-cut, a procedure which is cumbersome and which increases the danger of neurotrauma or nerve damage. Due to the thread which is of no use as far as mechanical strength is concerned, the outer diameter of the screw is unnecessarily large. During the healing process which can take several months, in the region of the zygapophyseal joints, a large number of forces act upon the screws and their bedding, transversely to the screw axis. Consequently, over time, this bedding can be destroyed by the sharp ridges of the thread. Furthermore, screws provide the temptation of excessive tightening. Because the thread of translaminar screws is pre-cut so as to be continuous, i.e. the thread continues in the spinous process and the subsequent lamina, excessive tightening of the screw may cause the spinous process to break off. Conventional translaminar vertebral-screw fixation is associated with a serious disadvantage in that due to the need for positioning the screws in the spinous process so that they cross in close proximity, and due to the limited space available in this position, placement of the second screw must already be considered before placing the first screw. Otherwise it may happen that only one screw is favourably placed from an anatomical and mechanical point of view. Furthermore, the spinous process is weakened by two screw channels crossing in close proximity. This can have a negative effect if an additional loadbearing element, e.g. a bone chip, is be jammed between the spinous processes. The protruding head of conventional screws used so far, prevents any embedded arrangement. Later on, it must be possible to remove the screws again.

It is the object of the present invention to form an osteosynthesis screw of the type mentioned in the introduction, that can be screwed-in in a way that is gentle to the bone, that provides security against axial movement and against rotational movement, and that will achieve an improvement in application techniques.

According to the invention it is proposed that the shaft has a section with a thread on the end section oriented towards the head, that the remaining section of the shaft up to the free end is without a thread, that the diameter of the head corresponds at least approximately to the outer diameter of the thread and comprises an inner notch arrangement for a tool, and that the section of the shaft with thread and/or the section of the shaft without thread is noncircular, of uniform thickness e.g. trilobular or polygonal, and/or comprises elevations and/or indentations.

By having a thread only in part of the shaft and by having a large section without a thread, with a larger core diameter, damage to the bone wall can be kept very slight. Thus the thread is provided only to prevent dislocation of the osteosynthesis screw in axial direction. When in addition the section with the thread and/or the threadless section is non-circular or similar, from the very beginning after setting the screw, positive locking between the bone material and the surface of the osteosynthesis screw is achieved by elastic adaptation of the elastically deformable bone and later by regrowing bone. In this way from the very beginning and increasingly thereafter, the new screw provides security against automatic unscrewing due to repetitive load changes, a problem occurring with conventional osteosynthesis screws. Furthermore, as a result of the special configuration of the head, the osteosynthesis screw according to the invention can be embedded, i.e. it can interact along its entire length with the bone components to be blocked, without protruding. In this way potentially dangerous fracture situations can be avoided which may well occur if there was a screw head to rest against a bone component, during screwing-in of the screw.

Since security against rotation of the osteosynthesis screw does not require great forces, positive locking by elastic deformation and by regrowing bone tissue is perfectly adequate. This also provides the option of subsequent removal of the osteosynthesis screw, because applying some force to the osteosynthesis screw in rotational direction will undo this positive locking without any problems.

The measures according to the invention make possible two techniques of application. Where there is sufficient space, the screws can be implanted in the conventional way, i.e. with the head exposed on the surface of the spinous process and with the screws crossing over in the spinous process. In the second option, which in many cases is the more favourable technique, first a shorter screw can be inserted, with its head embedded. The second screw can then be implanted without any regard to the position of the first screw. This technique provides the advantage in that it does not require any compromises regarding the most favourable anatomical and mechanical screw position. Both screws can be placed optimally.

With such a osteosynthesis screw it is advantageous if the thread of the shaft is self-tapping and/or self-cutting.

A particular embodiment provides for the thread-free section of the shaft to be cylindrical or conical, with the section of the shaft comprising the thread being non-circular, of uniform thickness e.g. trilobular or polygonal, and/or comprising elevations and/or indentations. To provide security against rotation it is perfectly adequate if only the short section of the thread is e.g. trilobular. In addition, screwing-in the osteosynthesis screw and thus production of the thread in the borehole of the bone can be facilitated. Such an embodiment is advantageous in that in the deeply screwed-in section of the osteosynthesis screw, bone material can only contact a cylindrical section; in other words no positive locking can occur which would hinder subsequent undoing by turning. This is advantageous for the subsequent undoing and unscrewing of the osteosynthesis screw.

In the context of the invention it is also possible to configure both the thread and the shaft cylindrically in this region, with the threadless section of the shaft adjacent to the thread being non-circular, of uniform thickness e.g. trilobular or polygonal, and/or comprising elevations and/or indentations. Such an arrangement is e.g. be imaginable if the deeper bone material or bone tissue is not too rigid, also in respect of the regrowing material. For security against rotation, this variant is also advantageous, whereby it must always be possible to unscrew the osteosynthesis screw. Here again, the threaded section has been provided for axial securing.

Furthermore it is proposed that the section of the shaft comprising the thread be located directly adjacent to the head. For use which is gentle on the bone it is particularly advantageous if the thread does not contact the bone too deeply along the bone. Thus for a large section, merely a type of sliding-in suffices when placing the osteosynthesis screw.

To make it possible for proper blocking of the bone components to be interconnected along the entire length of the borehole, it is provided for the outer diameter of the thread-free section of the shaft to correspond at least approximately to the core diameter of the section comprising the thread. This provides even support against the bore walls along the entire length of the osteosynthesis screw, with the thread additionally engaging the bore wall only to provide security against axial sliding.

Since even a short section of an engaging thread is sufficient to provide security against axial sliding of the osteosynthesis screw, it is proposed that the axial length of the section comprising the thread be shorter than the axial length of the thread-free section of the shaft.

Since as a result of the embeddable head of the osteosynthesis screw only an inner notch arrangement for a tool can be considered, particular attention must be paid to the necessity of subsequent unscrewing of the osteosynthesis screw. For it can happen time and again that already during insertion of the tool, bone material or similar enters the inner notch arrangement for a tool. It is thus proposed that at the head, at its deepest delimitation the inner notch arrangement for a tool provide an additional recess or a pocket-like indentation. In this way, a small accommodation space is created to accommodate such material which has inadvertently entered the inner notch arrangement for a tool, so as not to impede engagement of the tool.

A further embodiment provides for the head at its free end to comprise an annular collar whose diameter is smaller than the outer diameter of the head. This advantageous construction provides better handling of such osteosynthesis screws in combined action with respective tools, and also with any protective elements or covers.

So as not to cause any weakening of the cross-section, it is proposed that the axial length of the annular section be less than half the entire length, preferably less than a third of the entire length, of the head.

An advantageous embodiment provides for the annular collar to match an annular sleeve placed onto a tool; when in place said annular sleeve encompasses the annular collar of the head during the screwing process. This makes it possible to optimally retain in the tool the osteosynthesis screw to be screwed in, in other words, exact aiming with the osteosynthesis screw is achieved. By means of such an annular sleeve, the osteosynthesis screw can also be held captive in the tool until said osteosynthesis screw has been inserted in the borehole in the bone. In addition, the annular collar is kept free of impurities and bone deposits until the tool and thus also the sleeve are withdrawn, in this way keeping the sleeve free of impurities and bone deposits.

To enable easier insertion of the osteosynthesis screw in the prepared borehole, it is proposed that the free end of the thread-free section of the shaft comprise a section which e.g. tapers off in a truncated-cone shape or in a hemispherical shape.

An additional embodiment provides for a cover for closing off the inner notch arrangement for a tool, with said cover being able to be placed onto the head in a non-positive and/or positive way. In this way the free space of the inner notch arrangement for a tool can be kept free for subsequently necessary unscrewing of the osteosynthesis screw. The regrowing bone material can thus not enter the region of the inner notch arrangement.

In this context it is advantageous if the cover comprises an annular stay pointing towards the head, said stay being able to be placed onto the annular collar of reduced diameter at the head. This ensures optimal retention of the cover, and in addition, the annular collar is kept free of regrowing bone material. After removal of such a cover, the tool can immediately be applied, together with the annular sleeve.

It is advantageous if the outer diameter of the cover at least approximately corresponds to the outer diameter of the head. This makes it easier to place the cover after placement of the osteosynthesis screw, since in practice a part fitted to the borehole, is inserted. Of course, this also facilitates any subsequent removal of the cover.

If according to a further variant of the embodiment, viewed in axial direction, the cover comprises annular stays projecting to both sides, this provides the possibility of placing such a cover onto the free end of the head of the osteosynthesis screw, with the use of a tool. With the annular stay projecting to the other side, the end of a tool can be encompassed, said tool then being used to press the cover onto the head which is already embedded in the borehole.

In conjunction with the cover which has been placed on the head of the osteosynthesis screw after inserting said screw, an optimal solution for subsequent pulling off or removal of the cover is also proposed. This solution provides for the cover, at its centre, to comprise a predetermined breaking point and/or e.g. sections connected in sector-shape by way of predetermined breaking lines, for producing an opening when inserting a tool with a coneshaped or pyramid-shaped tip. Thus it is simple to insert a tool with which the cover is penetrated. This tool can then reach behind the cover, in the centre region, like a barb. By withdrawing the tool, the cover can be removed from the head. Subsequently it only requires insertion of the tool in the osteosynthesis screw, into the inner notch arrangement for a tool, and the osteosynthesis screw can be unscrewed. After the cover has been withdrawn, not only the inner notch arrangement for a tool but also the annular collar, are readily accessible without encountering any deposits.

If the outer limit of the cover comprises one or several groove-like indentations, this also ensures captive retention of said cover in the position in place on the head of the osteosynthesis screw. The regrowing bone material will immediately also engage these groove-like indentation(s), thus preventing subsequent axial movement in relation to the bone and thus also in relation to the osteosynthesis screw.

A further embodiment is characterised by a trunnion which at least partly fills-in a section of the borehole which remains free after embedded placement of the osteosynthesis screw, said trunnion being made from an elastic, histocompatible, non-absorbable material. In this way, access to the screw head is always ensured even if the osteosynthesis screw is to be removed after having been in place for a long time. In this way the clear area of the borehole can be prevented from filling up and thus practically being closed up by bone tissue entering.

A further embodiment is characterised by a tool insertable in the inner notch arrangement for a tool, of the osteosynthesis screw, with a sleeve coaxially arranged on said tool, said sleeve accommodating in a coaxially encompassing manner at least a large part of the axial length of the head of the osteosynthesis screw. This embodiment brings about optimal alignment and retention of the osteosynthesis screw when turning said screw in. This prevents any misalignment between the screw and the tool during screwing in.

Further characteristics and advantages are explained in the detailed description below, with reference to the drawings as follows:

FIG. 10 is a longitudinal section of a cover insertable in the head;

FIG. 11 is a sectional view of the region of the head with the cover inserted;

FIG. 12 shows a handling tool for inserting the cover, with a cover inserted at the free end of the tool;

FIG. 13 shows a tool for withdrawing the cover;

FIG. 14 shows a tool according to FIG. 13 in use after pushing through the cover but before withdrawing the cover;

FIG. 15 shows a further embodiment of a tool for screwing-in the osteosynthesis screw;

FIG. 16 shows another embodiment of a cover insertable in the head of a screw; and FIG. 17 shows a trunnion as used in the example according to FIG. 3.

Figure 1:
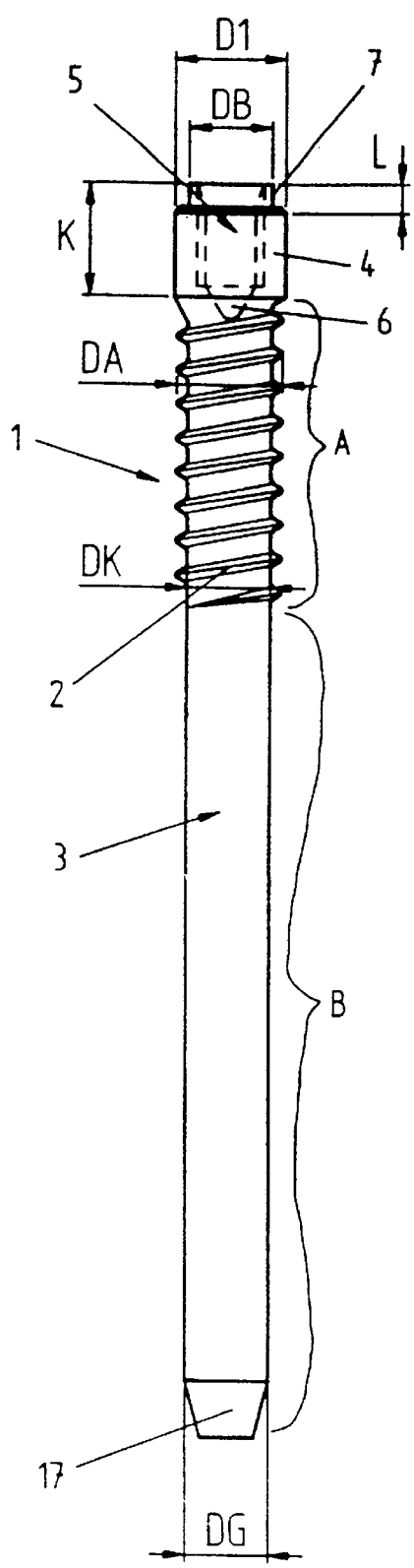
FIG. 1 is an enlarged view of an osteosynthesis screw.
Figure 2:
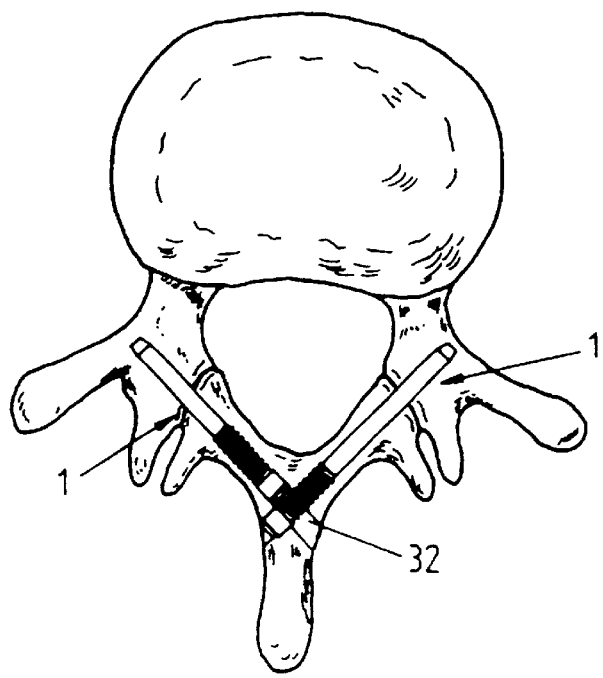
FIG. 2 is a top view of a vertebra with facet joints of the spine, showing the approximate position of the inserted osteosynthesis screws.

The osteosynthesis screw 1 shown in FIG. 1 is designed in particular for application in translaminar vertebral-screw fixation. This osteosynthesis screw 1 comprises a shaft 3 at least partially comprising a thread 2 and a head 4 formed at least at one of its ends and comprising a notch arrangement 5 for a tool. At its end section towards the head 4, the shaft 3 comprises a section A which has a thread 2. The remaining section B of the shaft 3 up to the free end is thread-free. The diameter DK of the head 4 corresponds at least approximately to the outer diameter DA of the thread 2. Furthermore, the head 4 comprises an inner notch arrangement 5 for a tool.

The thread-free section B of the shaft 3 is cylindrical, while section A of the shaft 3, comprising the thread 2, is of uniform thickness; in this particular case its cross-section is trilobular.

However, in principle, it is possible that section A of the shaft 3 with the thread 2 and/or section B of the shaft 3 without the thread is of uniform thickness e.g. trilobular or polygonal and/or comprises elevations and/or indentations. Thus thread 2 and shaft 3 could be cylindrical in shape in this area A, in which case the thread-free section B of shaft 3, adjoining section A with the thread 2, along its entire length or along only one or several partial sections is non-circular, of uniform thickness e.g. trilobular or polygonal, and/or comprises elevations and/or indentations. Advantageously, the thread 2 on shaft 3 is self-cutting and/or self-tapping.

Section A of shaft 3 comprising the thread 2 is arranged directly adjacent to the head 4. This osteosynthesis screw 1 is characterised by the outer diameter DG of the thread-free section of the shaft 3 corresponding at least approximately to the core diameter DK of the section A comprising the thread 2. In the embodiment shown, the axial length of section A comprising the thread 2 is shorter than the axial length of the thread-free section B of shaft 3.

It has already been mentioned that the head 4 of the osteosynthesis screw 1 comprises an inner notch arrangement 5 for a tool. To accommodate bone material or similar which has unintentionally entered the inner notch arrangement 5 for a tool, at its deepest delimitation, said inner notch arrangement for a tool provides an additional recess or a pocket-like indentation 6. At its free end, the head 4 comprises an annular collar 7 whose diameter DB is smaller than the outer diameter D1 of the head 4. The axial length L of the annular collar 7 is less than half the total length K, preferably less than a third of the total length K of the head 4. For further improved adhesion, the annular collar 7 can comprise a cover 18 incorporating ribbing or surface roughing. The nature of this annular collar 7 will be explained in more detail below. The free end of the thread-free section B of the shaft 3 comprises a section 17 which tapers off in a truncated-cone shape. This facilitates insertion of the osteosynthesis screw 1 in the prepared hole.

The osteosynthesis screw 1 can be made of metal, e.g. of stainless steel, titanium, tantalum, CoCr alloy or other metal. In particular, production using a composite material comprising polymers and respective reinforcement fibres or using ceramic materials is particularly advantageous. In the case of production from a composite material, the use of fibres and/or fibre-like components made of a material with high X-ray absorption is useful, e.g. made of tantalum, wolfram, gold, platinum or the like. The visibility to x-rays of the osteosynthesis screws used can be selected by a respective alignment and quantity of such fibres. The osteosynthesis screw described can also be used in other fields of medical technology where it is especially important that not too large a section along the length of the inserted fastener is impeded by thread formation, where securing against rotation and axial securing are important, and where the head should be embedded.

As a rule, first a hole which will subsequently accommodate a osteosynthesis screw 1 is drilled in the respective bone part, using a drill. In the case of translaminar screw fixation, preliminary drilling without a target device is possible, but not recommended. After the osteosynthesis screws 1 have been screwed into the small facet joints of the spine, the screws are entirely embedded. Due to the rapidly regrowing bone tissue, the trilobular cross-section of the thread 2 provides security against rotation. The thread 2 itself secures the screw against axial movement.

Figure 3:
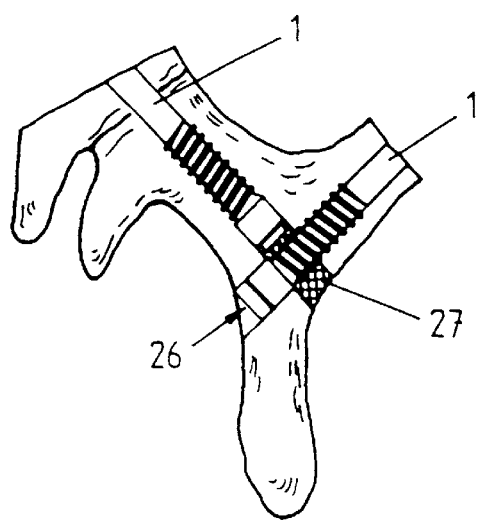
FIG. 3 is a top view, enlarged in comparison to FIG. 2, of a partial area of the neural arch of vertebra showing the approximate position of the inserted osteosynthesis screws, and with a trunnion inserted in a region of the borehole which region remains clear.
Figure 4:
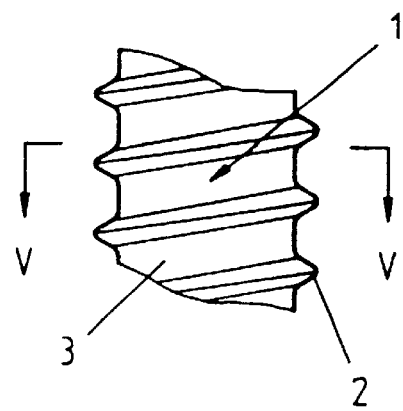
FIG. 4 shows the threaded shaft of the osteosynthesis screw, enlarged in comparison to FIG. 1.
Figure 5:
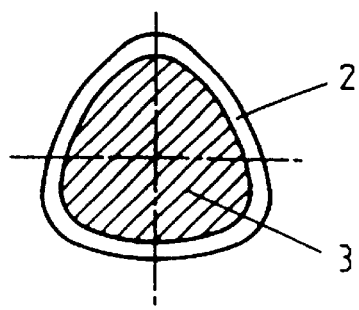
FIG. 5 shows a section along line V—V of FIG. 4.
Figure 6:
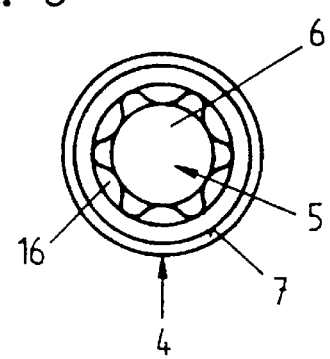
FIG. 6 is a top view of the head of the osteosynthesis screw.

As shown in FIG. 3, translaminar screw fixation also requires applications involving sinking the first osteosynthesis screw 1 to a different depth, so as to place the second osteosynthesis screw 1 in the best possible location too, without interference from the first screw. In this case, first a drill hole is made for the first screw which is to be inserted to a greater depth, and then said first screw is screwed in. Subsequently, the second drill hole is made. This second screw is not yet inserted at this stage. Instead, first, the section of the first borehole 32 which section remains clear behind the head of the screw is filled by means of a trunnion 27, as shown in FIG. 17. This trunnion can essentially be a cylindrical component with an extension 34 at its free end. The said extension can engage the inner notch arrangement 5 for a tool, of the head 4 of the osteosynthesis screw, so as to provide protection of said inner notch arrangement for a tool, against penetration by tissue material. This trunnion 27 comprises an elastic, histocompatible, non-absorbable material, e.g. silicon caoutchouc. However, the use of an elastic/plastic material is also possible. After inserting this trunnion 27, which due to the elastic material optimally engages the aperture of the inner notch arrangement 5 for a tool, of the screw, the section of the trunnion 27 which crosses the second drill hole is penetrated for example with an awl. The second screw can now be inserted. The second screw is thus inserted so as to cross the trunnion 27, or else laterally beside this trunnion, if the screws are not arranged in one plane or if they are not directly crossing. The length of the trunnion 27 may purposely be too large for most applications; in this case said trunnion is cut to length after placement of the second screw. In other words, the protruding part of the trunnion is cut off. If the second screw is only slightly embedded or not embedded at all, a type of cover 26 is placed on it. This cover 26 can be constructed in various ways. It is imaginable to provide for an embodiment similar to the embodiment according to FIG. 10 or else an embodiment according to FIG. 16 or an embodiment using the same material as that used with trunnion 27. In the case of an embodiment according to FIG. 16, a section 35 engaging the inner notch arrangement 5 for a tool, of the osteosynthesis screw 1, is provided which section for example comprises two parts which after insertion rest in an elastic or springy manner against the interior wall of the inner notch arrangement 5 for a tool. This cover 26 thus closes off the inner notch arrangement 5 for a tool of the osteosynthesis screw 1 and any region of the borehole which still remains free for accommodating the second osteosynthesis screw.

Figure 7:
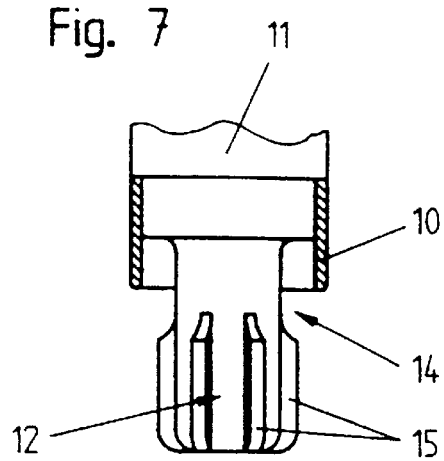
FIG. 7 is a lateral view of a tool for rotating the osteosynthesis screw.
Figure 9:
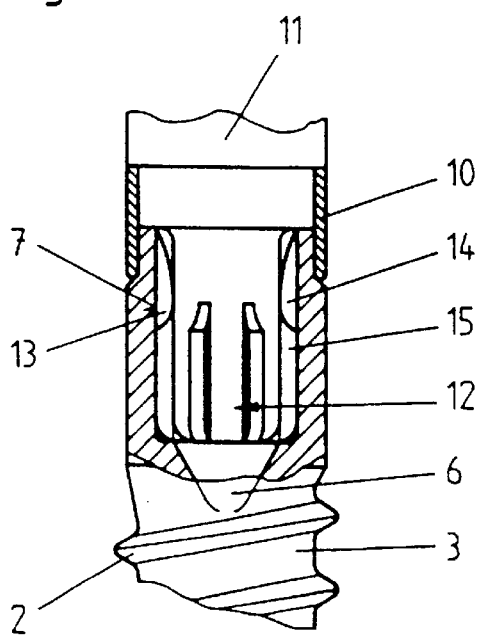
FIG. 9 shows a tool inserted in the head of the osteosynthesis screw.
Figure 8:
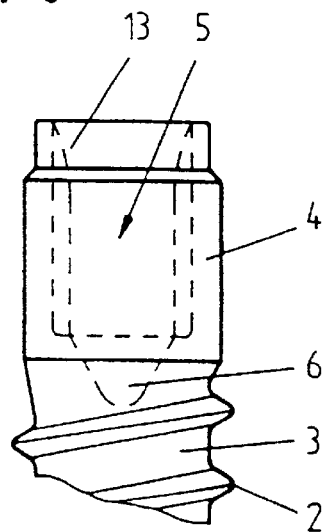
FIG. 8 is an enlarged view of the head region of the osteosynthesis screw.

As shown from FIGS. 7 to 9, the annular collar 7 is adapted to an annular sleeve 10 fitted to a tool 11, said annular sleeve encompassing the annular collar 7 of the head 4 during the screwing process. Thus the osteosynthesis screw 1 can be placed onto the tool 11 prior to the screw-in process. The said screw is then held axially aligned as a result of the notch arrangement 12 itself, and by the annular sleeve 10 arranged coaxially to said notch arrangement. The engagement ribs 15 of the notch arrangement 12 are shorter than the depth of the inner notch arrangement 5 for a tool, at the osteosynthesis screw 1, i.e. a circumferential groove 14 is formed at this location. This makes possible a particularly gentle introduction of force, even if it should happen that the notch arrangement 12 is not fully inserted in the inner notch arrangement 5 for a tool. The ribs of the notch arrangement 16 in the inner notch arrangement 5 for a tool comprise a bevel 13 towards their free end, thus allowing easier insertion of the tool into the notch arrangement 12.

FIGS. 10 to 12 show a cover 18 which can be placed in a non-positive and/or positive-locking way onto the head 4, for closing off the inner notch arrangement 5 for a tool. The cover 18 comprises an annular stay 19 pointing towards the head 4, said stay being able to be placed onto the annular collar 7 of reduced diameter DB at the head 4. The outer diameter D of the cover 18 at least approximately corresponds to the outer diameter D1 of the head 4. For the cover 18 to be easily placeable on the osteosynthesis screw 1 using a tool 20 or an extension 21 of such a tool 20, the cover 18 comprises annular stays 19 and 22 projecting in both axial directions. At its outer delimitation, the cover 18 can comprise one or several groove-like indentation(s) 23. After placement of the cover 18 on the head 4 of the osteosynthesis screw 1, fast regrowing bone tissue can also penetrate this groove-like indentation 23 or these groove-like indentations 23, thus additionally securing the position of the cover 18 in relation to the head 4.

FIGS. 13 and 14 show a particular embodiment of the cover 18 and a tool 24 that can be used for this purpose. In its centre, the cover 18 comprises a predetermined breaking point and/or e.g. sections, connected in sector-shape with predetermined breaking lines, for producing an opening when inserting a tool 24 with a cone-shaped or pyramid-shaped tip 25. Thus if after some time the osteosynthesis screw 1 is to be removed, i.e. unscrewed, the tool 4 can be inserted, with the tip 25 at the free end of this tool 24 penetrating the cover 18 at its centre. As a result of the barb-like shape of the tool 24, withdrawal of said tool results in removal of the cover 18 from the head 4 of the osteosynthesis screw 1. After removing the cover 18, the tool 11 can then simply be placed onto the notch 12 and the annular sleeve 10, since all these sections for engaging the tool 11 were closed off from the cover 18 and are now accessible again. Penetration of the cover is also possible directly by means of a screwdriver so that the osteosynthesis screw can be unscrewed without the cover having to be removed first.

The embodiment according to FIG. 15 provides a particular type of tool 11 for screwing-in the osteosynthesis screw 1. In this case the diameter of the head 4 of the screw can be somewhat smaller than the outer diameter of the thread 2. The tool 11 which can be inserted in the screw's inner notch arrangement 5 for a tool, is coaxially enclosed by a sleeve 28. This sleeve 28 accommodates in an encompassing manner at least a large part of the axial length of the head 4 of the screw, thus providing firm retention for the screw. In this way, axial alignment between screw and tool 11 is optimal. By means of a shoulder 33, the sleeve 28 is supported at the free end of the head 4. A projecting collar 29 or similar on the tool 11 provides an end stop for the rear end of the sleeve. Thus the sleeve 28 is always aligned in the same way in relation to the tool 11, thus ensuring constant engagement in the region of the inner notch arrangement for a tool. Instead of the arrangement using a collar, it is also imaginable to provide the tool 11 with a respective end stop, for example to provide an increased diameter from this end-stop region onward. In this case, for example the outer diameter of the sleeve 28 and the section of the tool following said sleeve, can be the same. In this particular design, the section 30 of the sleeve 28 directly encompassing the head 4 of the screw is somewhat thinner than the remaining section of the sleeve 28. In this way, section 30 does not account for much of the outer diameter so that the borehole which has to be made need not be significantly larger than the borehole for the shaft section of the screw. For improved insertion of the free end of the sleeve 28 in the region of the borehole it is advantageous if the free end of section 30 of the sleeve 28 comprises a chamfer 31.

For simpler placement without excessive radial forces in the bone region, the use of a tool according to FIG. 15 makes it possible to use a different drilling technique. First a borehole can be made which matches the region of the shaft of the screw. In this way exact selection of the required depth of the borehole is possible. However, for optimal placement of the screw 1, in particular in the context of a tool according to FIG. 15, a type of stepped borehole is useful. In this case, in a second step, a type of stepped drill is used. A cylindrical pin matched to the borehole diameter of the main borehole is shaped first; then follows a borehole section whose diameter matches the diameter of the sleeve 28 or an enlarged head of the screw.

Still further thread/shaft combinations are possible within the context of the invention. Special thread shapes can also be used. The use of two thread sections of different thread pitch is imaginable as is a thread section with a variable thread pitch. This would provide still further variants for security against rotation and against longitudinal movement.

What is claimed is:

1. An osteosynthesis screw, in particular for application in translaminar vertebral-screw fixation, with a shaft which at least in part comprises a thread and a head formed at least at one of its ends and comprising a notch arrangement for a tool, characterized in that the shaft (3) has a section (A) with a thread (2) on the end section oriented towards the head (4) and that the remaining section (B) of the shaft (3) up to the free end is without a thread (2), that the diameter (D1) of the head (4) corresponds at least approximately to the outer diameter (DA) of the thread (2) and comprises an inner notch arrangement (5) for a tool, and that at least one of the sections (A) of the shaft (3) with the thread (2) and the section (B) of the shaft (3) without the thread is non-circular and of uniform thickness.

2. The osteosynthesis screw according to claim 1, characterised in that the thread (2) of the shaft (3) is self-tapping or self-cutting.

3. The osteosynthesis screw according to claim 1 characterised in that the thread-free section (B) of the shaft (3) is cylindrical or conical, with section (A) of the shaft (3) comprising the thread (2) being non-circular, and of uniform thickness.

4. The osteosynthesis screw according to claim 1 characterised in that the thread (2) and the shaft (3) in this section (A) are cylindrical, with the threadless section (B) of the shaft (3) adjacent to the thread (2) being non-circular, and of uniform thickness.

5. The osteosynthesis screw according to claim 1 characterised in that section (A) of the shaft (3) comprising the thread (2) is located directly adjacent to the head (4).

6. The osteosynthesis screw according to claim 1 characterised in that the outer diameter (DG) of the thread-free section (B) of the shaft (3) at least approximately corresponds to the core diameter (DK) of the section (A) comprising the thread (2).

7. The osteosynthesis screw according to claim 1 characterised in that the axial length of the section (A) comprising the thread (2) is shorter than the axial length of the thread-free section (B) of the shaft (3).

8. The osteosynthesis screw according to claim 1 characterised in that at the head (4), at its deepest delimitation, the inner notch arrangement (5) for a tool comprises an additional recess or a pocket-like indentation (6).

9. The osteosynthesis screw according to claim 1 characterised in that the head (4) at its free end comprises an annular collar (7) whose diameter (DB) is smaller than the outer diameter-(D1) of the head (4).

10. The osteosynthesis screw according to claim 9, characterised in that the axial length (L) of the annular collar (7) is less than half the entire length (K), or less than a third of the entire length (K), of the head (4).

11. The osteosynthesis screw according to claim 9, characterised in that the annular collar (7) matches an annular sleeve (10) placed onto a tool (20), when in place said annular sleeve encompassing the annular collar (7) of the head (4) during the screwing process.

12. The osteosynthesis screw according to claim 1, characterised in that the free end of the thread-free section (B) of the shaft (3) comprises a section (17) which tapers off in a truncated-cone shape or in a hemispherical shape.

13. The osteosynthesis screw according to claim 1, characterised by a cover (18) for closing off the inner notch arrangement (5) for a tool, with said cover being able to be placed onto the head (4) in a non-positive or positive manner.

14. The osteosynthesis screw according to claim 13, characterised in that the outer diameter (D) of the cover (18) at least approximately corresponds to the outer diameter (D1) of the head (4).

15. The osteosynthesis screw according to claim 13, characterised in that the cover (18) at its outer limit comprises groove-like indentations (23).

16. The osteosynthesis screw according to claim 1, characterised by a tool (11) insertable in the inner notch arrangement (5) for a tool, of the osteosynthesis screw (1), with a sleeve (28) coaxially arranged on said tool, said sleeve accommodating in a coaxially encompassing manner at least a large part of the axial length of the head (4) of the osteosynthesis screw (1).

17. The screw of claim 1, wherein the section (A) or the section (B) of the shaft is trilobular or polygonal.

18. The screw of claim 1, wherein both the section (A) and the section (B) of the shaft are trilobular or polygonal.

19. An osteosynthesis screw, in particular for application in translaminar vertebral-screw fixation, with a shaft which at least in part comprises a thread and a head formed at least at one of its ends and comprising a notch arrangement for a tool, characterized in that the shaft (3) has a section (A) with a thread (2) on the end section oriented towards the head (4) and that the remaining section (B) of the shaft (3) up to the free end is without a thread (2), that the diameter (D1) of the head (4) corresponds at least approximately to the outer diameter (DA) of the thread (2) and comprises an inner notch arrangement (5) for a tool, and that at least one of the sections (A) of the shaft (3) with the thread (2) and the section (B) of the shaft (3) without the thread is non-circular and of uniform thickness, in that the screw has a cover (18)

for closing off the inner notch arrangement (5) for a tool, with said cover being able to be placed onto the head (4) in a non-positive or positive manner and in that the cover (18) comprises an annular stay (19) pointing towards the head (4), said stay being able to be placed onto the annular collar (7) of reduced diameter (DB) at the head (4).

20. An osteosynthesis screw, in particular for application in translaminar vertebral-screw fixation, with a shaft which at least in part comprises a thread and a head formed at least at one of its ends and comprising a notch arrangement for-a tool, characterized in that the shaft (3) has a section (A) with a thread (2) on the end section oriented towards the head (4) and that the remaining section (B) of the shaft (3) up to the free end is without a thread (2), that the diameter (D1) of the head (4) corresponds at least approximately to the outer diameter (DA) of the thread (2) and comprises an inner notch arrangement (5) for a tool, and that at least one of the sections (A) of the shaft (3) with the thread (2) and the section (B) of the shaft (3) without the thread is non-circular and of uniform thickness, in that the screw has a cover (18) for closing off the inner notch arrangement (5) for a tool, with said cover being able to be placed onto the head (4) in a non-positive or positive manner and in that the cover (18) comprises annular stays (19, 22) projecting in both axial directions.

21. An osteosynthesis screw, in particular for application in translaminar vertebral-screw fixation, with a shaft which at least in part comprises a thread and a head formed at least at one of its ends and comprising a notch arrangement for a tool, characterized in that the shaft (3) has a section (A) with a thread (2) on the end section oriented towards the head (4) and that the remaining section (B) of the shaft (3) up to the free end is without a thread (2), that the diameter (D1) of the head (4) corresponds at least approximately to the outer diameter (DA) of the thread (2) and comprises an inner notch arrangement (5) for a tool, and that at least one of the sections (A) of the shaft (3) with the thread (2) and the section (B) of the shaft (3) without the thread is non-circular and of uniform thickness, that the screw has a cover (18) for closing off the inner notch arrangement (6) for a tool, with said cover being able to be placed onto the head (4) in a non-positive or positive manner and that the cover (18) at its centre comprises a predetermined breaking point or sections connected in sector-shape by way of predetermined breaking lines, for producing an opening when inserting a tool (24) with a cone-shaped or pyramid-shaped tip (25).

22. An osteosynthesis screw, in particular for application in translaminar vertebral-screw fixation, with a shaft which at least in part comprises a thread and a head formed at least at one of its ends and comprising a notch arrangement for a tool, characterized in that the shaft (3) has a section (A) with a thread (2) on the end section oriented towards the head (4) and that the remaining section (B) of the shaft (3) up to the free end is without a thread (2), that the diameter (D1) of the head (4) corresponds at least approximately to the outer diameter (DA) of the thread (2) and comprises an inner notch arrangement (5) for a tool, and that at least one of the sections (A) of the shaft (3) with the thread (2) and the section (B) of the shaft (3) without the thread is non-circular and of uniform thickness, and characterised by a trunnion (27) which at least partly fills-in a section of the borehole (32) which remains free after embedded placement of the osteosynthesis screw (1), said trunnion being made from an elastic, histocompatible, non-absorbable material.

\* \* \* \* \*